United States Patent
Hollunder et al.

(10) Patent No.: US 10,132,789 B2
(45) Date of Patent: Nov. 20, 2018

(54) APPARATUS AND METHOD FOR DETECTING GAS

(71) Applicant: Maschinenfabrik Reinhausen GmbH, Regensburg (DE)

(72) Inventors: Sebastian Hollunder, Schmitten (DE); Martin Kubiczek, Hofheim (DE); Juergen Schuebel, Overursel (DE); Karsten Viereck, Regensburg (DE)

(73) Assignee: MASCHINENFABRIK REINHAUSEN GMBH, Regensburg (DE)

( * ) Notice: Subject to any disclaimer, the term of this patent is extended or adjusted under 35 U.S.C. 154(b) by 63 days.

(21) Appl. No.: 15/032,085

(22) PCT Filed: Nov. 17, 2014

(86) PCT No.: PCT/EP2014/074745
§ 371 (c)(1),
(2) Date: May 17, 2016

(87) PCT Pub. No.: WO2015/074990
PCT Pub. Date: May 28, 2015

(65) Prior Publication Data
US 2016/0266085 A1    Sep. 15, 2016

(30) Foreign Application Priority Data
Nov. 20, 2013    (DE) .......................... 10 2013 112 823

(51) Int. Cl.
*G01N 33/28*    (2006.01)
*G01N 25/14*    (2006.01)

(52) U.S. Cl.
CPC ......... *G01N 33/2841* (2013.01); *G01N 25/14* (2013.01)

(58) Field of Classification Search
CPC .......................... G01N 25/14; G01N 33/2841
See application file for complete search history.

(56) References Cited

U.S. PATENT DOCUMENTS 3,926,561 A * 12/1975 Lucero .................. B01D 53/22
                                                          422/83
4,058,373 A * 11/1977 Kurz .................. G01N 33/2841
                                                          73/19.1
(Continued)

FOREIGN PATENT DOCUMENTS

DE            254827 B      3/1988
DE      102010008066 B      3/2011
(Continued)

OTHER PUBLICATIONS

Pharas, Kunal, and Shamus McNamara. "Knudsen pump driven by a thermoelectric material." Journal of Micromechanics and Microengineering 20.12 (2010): 125032.*
(Continued)

*Primary Examiner* — Lisa Caputo
*Assistant Examiner* — Punam Roy
(74) *Attorney, Agent, or Firm* — Andrew Wilford

(57) ABSTRACT

An apparatus (1) for detecting gas (4) in a high-voltage device (3) filled with an insulating medium (2) comprises an inlet (5) for introducing a carrier gas (16) and an outlet (6) for discharging a carrier gas (16); at least one gas sensor (12) for detecting a gas (4); a first pump (9) for conveying the carrier gas (16) in the apparatus (1); a membrane (13) which at least consists of at least one semipermeable material, is at least partially surrounded by the insulating medium (2) and is at least partially subjected to a flow of the carrier gas (16); a second pump (10) for conveying the carrier gas (16) into the apparatus (1) and for conveying the carrier gas (16) out of the apparatus (1); wherein there is no valve which can be
(Continued)

used to convey the carrier gas (16) into the apparatus (1) or out of the apparatus (1).

19 Claims, 3 Drawing Sheets

(56) References Cited

U.S. PATENT DOCUMENTS

| | | | | |
|---|---|---|---|---|
| 4,444,040 | A | * | 4/1984 | Sakai ............... G01N 33/2841 73/19.02 |
| 4,764,344 | A | | 8/1988 | Knab |
| 4,939,405 | A | * | 7/1990 | Okuyama ............ F04B 43/046 310/317 |
| 5,400,641 | A | * | 3/1995 | Slemon .................. G01N 1/26 706/20 |
| 6,037,592 | A | * | 3/2000 | Sunshine ........... G01N 21/3504 250/343 |
| 6,391,096 | B1 | | 5/2002 | Waters |
| 6,526,805 | B1 | | 3/2003 | Babes-Dornea |
| 8,028,561 | B2 | * | 10/2011 | Herz ................. G01N 33/2841 73/19.12 |
| 8,075,675 | B2 | | 12/2011 | Mahoney |
| 8,442,775 | B2 | | 5/2013 | Santos |

FOREIGN PATENT DOCUMENTS

| | | |
|---|---|---|
| EP | 233922 A | 9/2010 |
| JP | 57156536 B | 9/1952 |

OTHER PUBLICATIONS

Y. Qin and Y. B. Gianchandani, "A facile, standardized fabrication approach and scalable architecture for a micro gas chromatography system with integrated pump," 2013 Transducers & Eurosensors XXVII: The 17th International Conference on Solid-State Sensors, Actuators and Microsystem, Barcelona, Jun. 16-20, 2013, pp. 2755-2758.*

Woias, Peter. "Micropumps-past, progress and future prospects." Sensors and Actuators B: Chemical 105.1 (2005): 28-38.*

Badman, Ethan R., and R. Graham Cooks. "Miniature mass analyzers." Journal of mass spectrometry 35.6 (2000): 659-671.*

Olsson, Anders, Göran Stemme, and Erik Stemme. "A valve-less planar fluid pump with two pump chambers." Sensors and Actuators A: Physical47.1-3 (1995): 549-556.*

Valve. (1992). In C. G. Morris (Ed.), Academic Press Dictionary of Science and Technology (4th ed.). Oxford, UK: Elsevier Science & Technology. Retrieved from <http://search.credoreference.com/content/entry/apdst/valve/0?institutionId=743>.*

Stemme, Erik, and Göran Stemme. "A valveless diffuser/nozzle-based fluid pump." Sensors and Actuators A: physical 39.2 (1993): Abstract.*

* cited by examiner

APPARATUS AND METHOD FOR DETECTING GAS

CROSS REFERENCE TO RELATED APPLICATIONS

This application is the US-national stage of PCT application PCT/EP2014/074745 filed 17 Nov. 2014 and claiming the priority of German patent application 102013112823.8 itself filed 20 Nov. 2013.

FIELD OF THE INVENTION

The invention relates to an apparatus and to a method for detecting gas in a high-voltage apparatus filled with an insulating medium, particularly high-voltage transformers.

BACKGROUND OF THE INVENTION

WO 2011/120113 [U.S. Pat. No. 8,442,775] describes a system and a method for monitoring gases in power transformers cooled by oil. In that case, the system consists of a rod and a main housing. The rod has two conduits running in the interior and is positioned in the oil of the power transformer. The conduits are connected together by two oil chambers and a pump so that the oil is sucked from the power transformer via a conduit to the first oil chamber and can be subsequently introduced by the second oil chamber through the other conduit back into the power transformer. The pump is in that case provided in a conduit section between the oil chambers. An additional region with a temperature detector and a moisture sensor is present in front of the pump. The two oil chambers have a wall consisting of a semipermeable material. Gases present in the oil of the power transformer can migrate through this wall into the interior of the main housing. An additional gas sensor detects the gases that collect in the main housing of the system. In addition, two valves each with a respective filter are provided at the housing. One of the valves is used for sucking air from the environment by a pump. The air is expelled from the interior of the main housing through the second valve. The system is controlled by a control.

This known system is of very complicated construction. The multiplicity of individual parts used means that the system is not only expensive, but also maintenance-intensive. The valves for the air exchange wear particularly quickly and thus form a weak point in the system. The flatly constructed membrane can rupture particularly quickly in the case of a sudden pressure rise and especially at the time of evaluation of the carrier gas.

U.S. Pat. No. 6,526,805 describes an apparatus for continuous analysis and measurement of the content of gas components in an insulating liquid substantially on a real-time basis. This apparatus comprises a gas extraction unit for separation of the gases from the liquid, an infrared gas analyzer for determining the concentration of the individual gas components, a gas pump for circulating the gases to the gas extraction unit in a closed loop and a calibrating device for the infrared gas analyzer. The gas extraction unit comprises a gas-permeable polymer membrane and a gas chamber with a gas flow inlet and a gas flow outlet. The infrared gas analyzer comprises an infrared source, a gas cell with a gas inlet and gas outlet and a quad-detector with extremely narrow-band optical infrared filters. The calibrating device comprises a valve device for flushing out the gas components with air and for resetting the infrared source to zero. The valve device comprises a first three-way valve that is seated between the gas pump and the gas extraction unit, and a second three-way valve that is seated between the gas cell and the gas pump.

U.S. Pat. No. 8,075,675 describes an apparatus for extraction of gas from a liquid. This apparatus comprises a housing, a separating membrane in the housing, a porous membrane support, an oil pump, a gas pump, a gas distributor and an analyzing instrument. The housing defines a fluid path and a gas path that is isolated from the fluid path, and has an inlet to the fluid path, an outlet from the fluid path, an inlet to the gas path and an outlet from the gas path. The separating membrane separates the fluid path from the gas path and comprises a fluorosilicone element that is impermeable to the liquid and permeable to the gas. The separating membrane has a first side facing the fluid path and a second side facing the gas path. The separating membrane forms a flattened disk that is thicker at the edge and thinner in the center. The membrane support faces toward the first side of the separating membrane. The fluid path contains the first side of the separating membrane. The oil pump conveys the liquid through the fluid path. The gas pump conveys a carrier gas and the gas that is released from the liquid, through the gas path. The analyzing instrument is connected with the gas path by the gas distributer. The gas distributor is described in detail in U.S. Pat. No. 6,391,096 and comprises seven control valves.

OBJECT OF THE INVENTION

The object of the invention is to provide an apparatus for detecting gas molecules in a high-voltage apparatus filled with insulating medium, which apparatus is constructed to be economic, maintenance friendly and wear-free, and to indicate a method for detecting gases in a high-voltage apparatus filled with liquids, which method ensures reliable operation of the apparatus.

SUMMARY OF THE INVENTION

This object is fulfilled by the subjects of the independent claims. Advantageous developments are described in the subclaims.

In accordance with a first aspect the invention proposes an apparatus for detecting gas in a high-voltage apparatus filled with an insulating medium, comprising:
an inlet for taking in and an outlet for discharging a carrier gas;
at least one gas sensor for detecting a gas;
a first pump for moving the carrier gas in the apparatus;
a membrane consisting of at least one semipermeable material and that is at least partly surrounded by the insulating medium and at least partly exposed to a flow of the carrier gas; and
a second pump for moving the carrier gas through the apparatus and for moving the carrier gas out of the apparatus; wherein
there is no valve through which the carrier gas can be conveyed into the apparatus or out of the apparatus.

Through the use of two pumps and the omission of valves the proposed apparatus is particularly wear-free and thus maintenance-friendly. A further advantage resides in the fact that not the insulating medium, but the carrier gas is circulated. It is thereby possible to introduce fresh carrier gas into the apparatus prior to the enrichment and detection and to discharge it from the apparatus after the detection.

The high-voltage apparatus can be constructed in desired mode and manner according to requirements, for example as a high-voltage transformer, a power transformer, an on-load tap changer, a power switch, a capacitor lead-through or other oil-filled electrical equipment.

The insulating medium can be constructed in desired mode and manner according to requirements, for example as insulating oil or ester fluid.

The gas to be detected can be formed in any desired mode and manner according to requirements and for example contain at least one hydrocarbon compound and/or other gas molecules and/or other gas atoms.

The semipermeable membrane can be constructed in any desired mode and manner according to requirements and can consist for example at least partly of Teflon.

The pumps can be constructed in any desired mode and manner according to requirements, for example as diaphragm pumps.

It can be provided that the inlet has a first conduit.

A filter is preferably seated in the conduit.

It can be provided that the membrane has an at least partly tubular and/or at least partly hose-like construction.

It can be provided that the membrane has an at least partly spiral and/or at least partly meandering and/or at least partly helical configuration.

It can be provided that the outlet has a second conduit.

The second pump is preferably provided in the second conduit, but it can also be provided in the first conduit.

Provision can be made for a measuring chamber in which the gas sensor is provided.

It can be provided that at least one thermoelement and/or at least one temperature sensor is or are provided in the measuring chamber.

It can be provided that the temperature sensor and the thermoelement are connected with a controller; and the thermoelement is controlled on the basis of the measurements of the temperature sensor.

Provision can be made for the measuring chamber to be connected with the first conduit and, by the membrane and the second conduit, with the outlet.

It can be provided that the measuring chamber is provided between the first conduit and the membrane.

It can be provided that during operation of the first pump the second pump blocks flow and during operation of the second pump the first pump blocks flow.

It can be provided that the thermoelement is constructed as a Peltier element.

It can be provided that the measuring chamber in the interior is lined with an inert material, platinum or gold.

Provision can be made for the second pump to be seated in the first conduit or in the second conduit.

It can be provided that if the second pump is seated in the first conduit then it has an aspect ratio that is greater than the second conduit and/or greater than 100, 200, 500, 1000, 2000, 5000 or 10,000 and/or it has a flow resistance that is greater than that of the second conduit and/or that corresponds with that of a conduit with a constant inner diameter and an aspect ratio greater than 100, 200, 500, 1000, 2000, 5000 or 10,000;

if the second pump is seated in the second conduit then it has an aspect ratio that is greater than the first conduit and/or greater than 100, 200, 500, 1000, 2000, 5000 or 10,000 and/or it has a flow resistance that is greater than that of the first conduit and/or that corresponds with that of a conduit with a constant inner diameter and an aspect ratio greater than 100, 200, 500, 1000, 2000, 5000 or 10,000.

The aspect ratio of a conduit is in that case the ratio of its length to its inner diameter.

Each conduit can be constructed in any desired mode and manner according to requirements and have for example a constant internal diameter over its length. Alternatively, at least one throttle or nozzle can be seated in a conduit with a smaller aspect ratio and is preferably dimensioned in such a way that the flow resistance of this conduit corresponds with a conduit with one of the indicated larger aspect ratios.

Provision can be made for the first pump to be seated in a first connecting conduit connecting an outlet of the measuring chamber with an inlet of the membrane or in a second connecting conduit connecting an outlet of the membrane with an inlet of the measuring chamber.

It can be provided that the first conduit opens between the first pump and the membrane into a first connecting conduit that connects an outlet of the measuring chamber with an inlet of the membrane, or opens between the first pump and the measuring chamber into a second connecting conduit, that connects an outlet of the membrane with an inlet of the measuring chamber.

According to a second aspect the invention proposes a method for detecting gas in a high-voltage apparatus filled with an insulating medium, preferably by means one of the apparatuses proposed in accordance with the first aspect, wherein in a first step a measuring chamber is flushed with a carrier gas in that the carrier gas is conveyed by a second pump into the measuring chamber and out of the measuring chamber without in that case flowing through a valve;

in a second step after the first step the carrier gas is conveyed by a first pump out of the measuring chamber, through a membrane and into the measuring chamber and in that case gas, that has accumulated in the carrier gas flowing against the membrane, is detected in the measuring chamber; and the membrane consists at least of at least one semipermeable material and is surrounded at least partly by the insulating medium.

It can be provided that during the flushing the carrier gas is sucked through a first conduit, conveyed through the measuring chamber and the membrane and purged through a second conduit.

Provision can be made for the carrier gas to be drawn in by a filter.

It can be provided that the amount and/or kind of gas in the measuring chamber is or are determined before and/or after the carrier gas was conveyed out.

It can be provided that the amount and/or kind of the gas in the measuring chamber is or are determined before and/or after the carrier was conveyed.

One of the proposed methods can be carried out for example by any of the proposed apparatuses.

For preference, each of the proposed apparatuses is constructed in such a way and/or serves the purpose and/or is suitable for the purpose that it carries out and/or can carry out one of the proposed methods.

The explanations and clarifications with respect to one of the aspects of the invention, particularly to individual features of this aspect, also correspondingly apply in analogous manner to the other aspects of the invention.

BRIEF DESCRIPTION OF THE DRAWING

Embodiments of the invention are explained in more detail in the following by example with reference to the accompanying drawings. However, the individual features evident therefrom are not confined to the individual forms of embodiment, but can be connected and/or combined with further above-described individual features and/or with individual features of other forms of embodiment. The details in the drawings are merely explanatory and not to be understood as limiting. The reference numerals contained in the claims are not to restrict the scope of protection of the invention in any way, but refer merely to the forms of embodiment shown in the drawings.

In the drawings.

Figure 1:
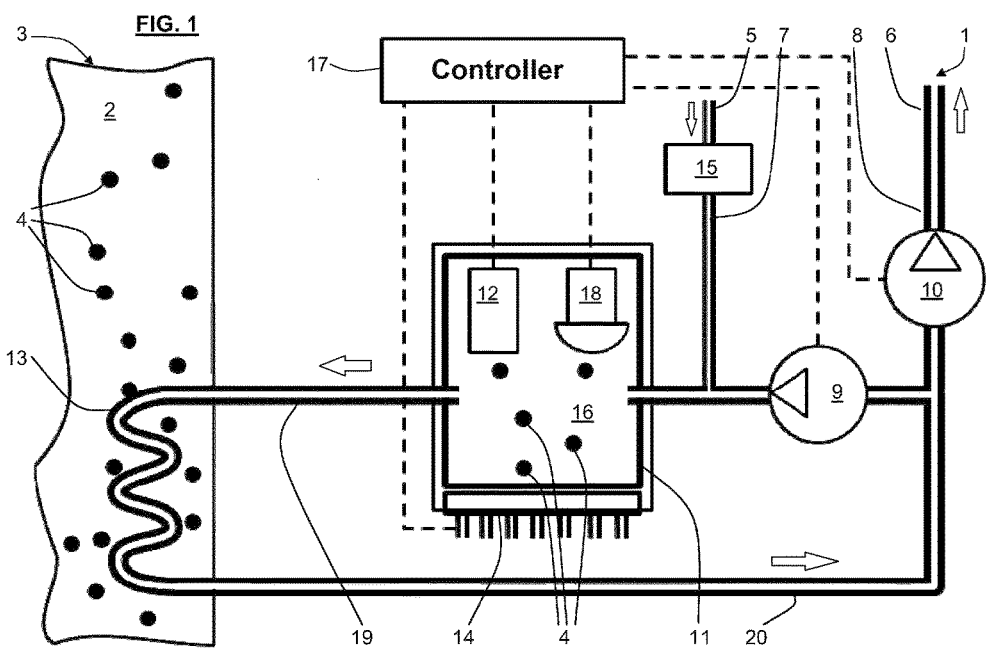
FIG. 1 shows a first embodiment of an apparatus for detecting gas.

Identical reference numerals are used the same or equivalent elements of the invention. Moreover, for the sake of clarity only reference numerals required for description of the respective drawing are illustrated in the individual drawings. The illustrated embodiments represent merely examples of what the apparatus according to the invention or the method according to the invention is or can be and thus do not represent a definitive limitation of the invention.

SPECIFIC DESCRIPTION OF THE INVENTION

A first embodiment of an system 1 for detection of gas molecules, ions or gases 4 in a high-voltage apparatus 3 filled with a liquid or an insulating medium 2, is schematically illustrated in FIG. 1. The high-voltage apparatus 3 can be a high-voltage transformer, a power transformer, an on-load tap changer, a power switch or a capacitor leadthrough. The system 1 comprises a membrane or capillary 13 consisting of at least one semipermeable material and of tubular or hose-like construction. The tubular membrane 13 can be shaped as desired, for example as a spiral and/or a helix and/or as a meander. By virtue of this advantageous form of the membrane 13 it is suitable for particularly high pressures. The membrane 13 is disposed in the high-voltage apparatus 3 or at least in a part of the high-voltage apparatus accessible to the insulating medium 2. The membrane 13 can thus be in a Buchholz relay, a conduit of the cooling system, etc. By virtue of the tubular construction and the material that is gas-permeable (semipermeable) in one direction, molecules of the gas 4 can pass into a circulation path of the system 1.

The membrane 13 is connected at one end forming its inlet by a first connecting conduit 19 with the outlet of a measuring chamber 11 and at another end forming forms its outlet by a second connecting conduit 20 with the inlet of the measuring chamber 11. The measuring chamber 11 comprises a thermoelement 14 that is for example a Peltier element that controls the temperature inside the measuring chamber 11. In addition, a gas sensor 12 and a temperature sensor 18 are provided in the measuring chamber 11.

The measuring chamber 11 is lined or coated internally with an inert material such as for example gold. This coating offers the advantage that the gases 4 do not deposit or condense in the interior and are non-reproducibly absorbed, in that case being able to enter into at least one polar physical bond and thus be absent in the overall gas balance, and false values by comparison with a laboratory analysis would be measured.

In addition, the measuring chamber 11 is connected with an intake 5 by a first conduit 7 that opens into the second connecting conduit 20. A filter 15 is provided upstream of the inlet 5. The first conduit 7 has a particularly high ratio between the length and flow cross-section. As a result pressure inside the system 1 corresponds with the pressure in the environment from which a carrier gas 16 is used. Since the pressure inside the high voltage apparatus 3 is always higher than the pressure of the environment and thus also the pressure in the device, the gases released into the insulating medium 2 pass into the flow path of the system 1 via the semipermeable membrane 13.

The measuring chamber 11 is additionally connected with a first pump 9 that is seated in the second connecting conduit 20 between the membrane 13 and the first conduit 7. This conveys the carrier gas 16 through the connecting conduits 19, 20, the measuring chamber 11 and the membrane 13, so that a circuit arises and the carrier gas 16 is enriched with the gases 4 from the insulating medium 2. In switched-off state, the first pump 9 blocks flow.

The system 1 additionally comprises a second pump 10 that on one side is connected with an outlet 6 by a second conduit 8 that opens into the second connecting conduit 20 between the membrane 13 and the first pump 9, and on the other side with the inlet 5 by the first conduit 7, the measuring chamber 11 and the membrane 13. In addition, in the switched-off state the second pump 10 takes over the function of a closed valve. During operation of the first pump 9 the second pump 10 is always switched off. During operation of the second pump 10, the first pump 9 is switched off.

If the first pump 9 is now switched on, a repeated conveying or circulation of the carrier gas 16 through the measuring chamber 11 and the membrane 13 takes place. In that case, the carrier gas 16 is enriched with the gases 4 that migrate through the semipermeable membrane 13 and thus release from the insulating medium 2, until the quantity of gases 4 to be taken up by the carrier gas 16 no longer significantly increases.

If the second pump 10 is switched on, an exchange of the carrier gas 16 in the system 1 takes place. This is sucked in by the inlet 5 and passed on via the measuring chamber 11 and the membrane 13 to the outlet 6. The gas sensor 12, temperature sensor 18 and thermoelement 14 in the measuring chamber 11 as well as the first and second pumps 9, 10 are connected with a central controller 17. The control of the thermoelement 14 is carried out on the basis of the measurements of the temperature sensor 18.

Figure 2:
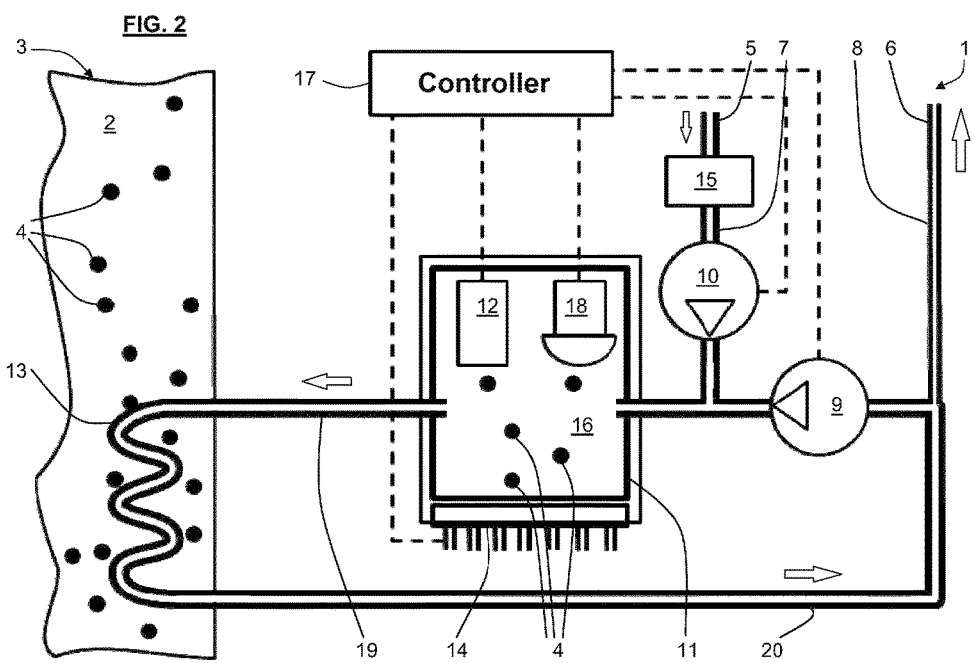
FIG. 2 shows a second embodiment of the apparatus.

A second embodiment of the system 1 is schematically illustrated in FIG. 2. This embodiment is similar to the first embodiment so that in the following primarily the differences are explained in more detail.

In this embodiment the second pump 10 is seated, not as in the first embodiment in the second conduit 8, but in the first conduit 7 and is consequently connected on one side with the inlet 5 and on the other side by the measuring chamber 11, the membrane 13 and the second conduit 8 with the outlet 6. In addition, in distinction from the first embodiment not the first conduit 7, but the second conduit 8 has a particularly high aspect ratio between the intrinsic length and the cross-section.

Figure 3:
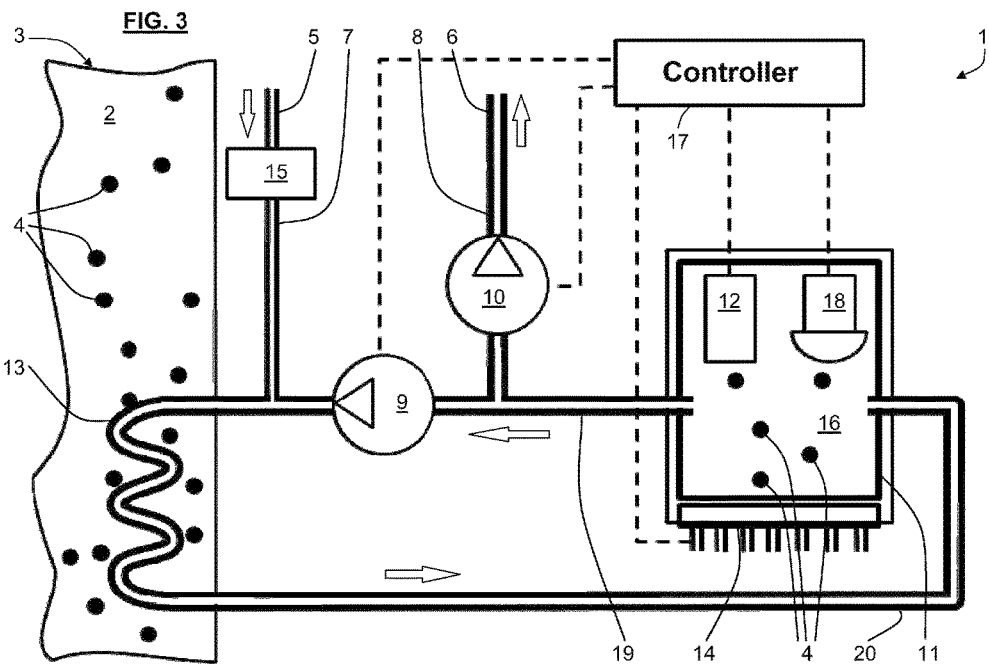
FIG. 3 shows a third embodiment of the apparatus.

A third embodiment of the system 1 is schematically illustrated in FIG. 3, this embodiment is similar to the first embodiment, so that primarily the differences are explained in more detail in the following.

In this embodiment the first pump 9 is seated not in the second connecting conduit 20 as in the case of the first embodiment, but in the first connecting conduit 19. Moreover, the first conduit 7 opens between the first pump 9 and the membrane 13 and the second conduit 8 opens between the measuring chamber 11 and the first pump 9 into the first connecting conduit 19.

For the flushing, the second pump 10 consequently inducts the carrier gas by the inlet 5 and conveys it through the filter 15, the first conduit 7, the downstream part of the first connecting conduit 19, the membrane 13, the second connecting conduit 20, the measuring chamber 11 and the upstream part of the first connecting conduit 19 to the outlet 6. Consequently, for the enrichment the first pump 9 circulates the carrier gas through the downstream part of the first connecting conduit 19, the membrane 13, the second connecting conduit 20, the measuring chamber 11 and the upstream part of the first connecting conduit 19.

Figure 4:
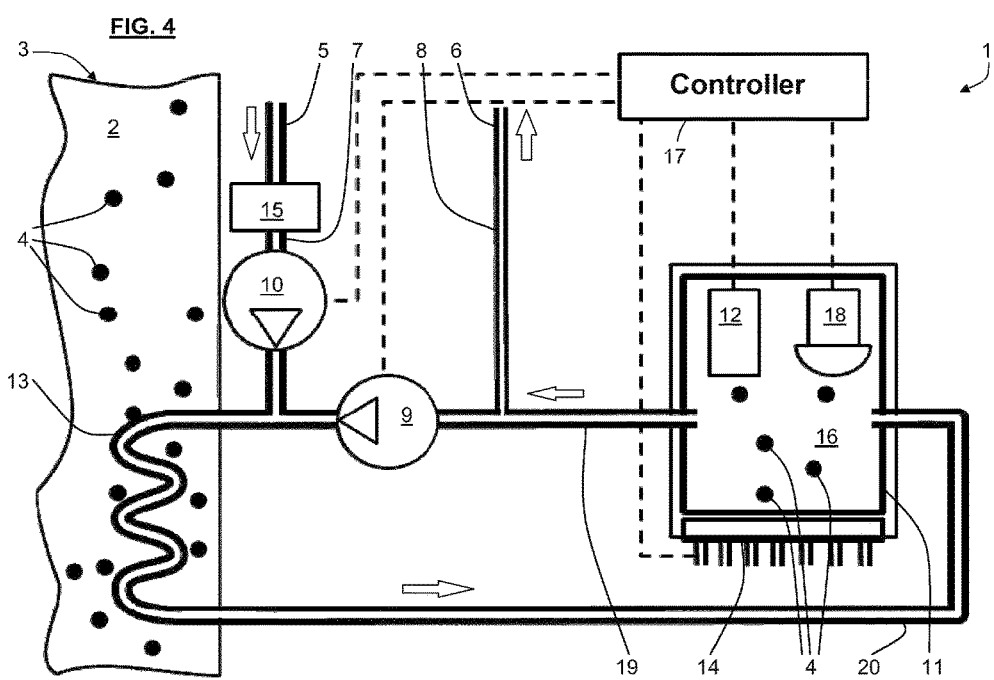
FIG. 4 shows a fourth embodiment of the apparatus.

A fourth embodiment of the system 1 is schematically illustrated in FIG. 4. This embodiment is similar to the third embodiment, so that primarily the differences are explained in more detail in the following.

In this embodiment the second pump 10 is seated not in the second conduit 8 as in the case of the third embodiment, but in the first conduit 7 and consequently is connected on one side with the inlet 5 and on the other side by the membrane 13, the measuring chamber 11 and the second conduit 8 with the outlet 6. Moreover, not the first conduit 7 as in the case of third embodiment, but the second conduit 9 has a particularly high aspect ratio between the intrinsic length and the cross-section.

Figure 5:
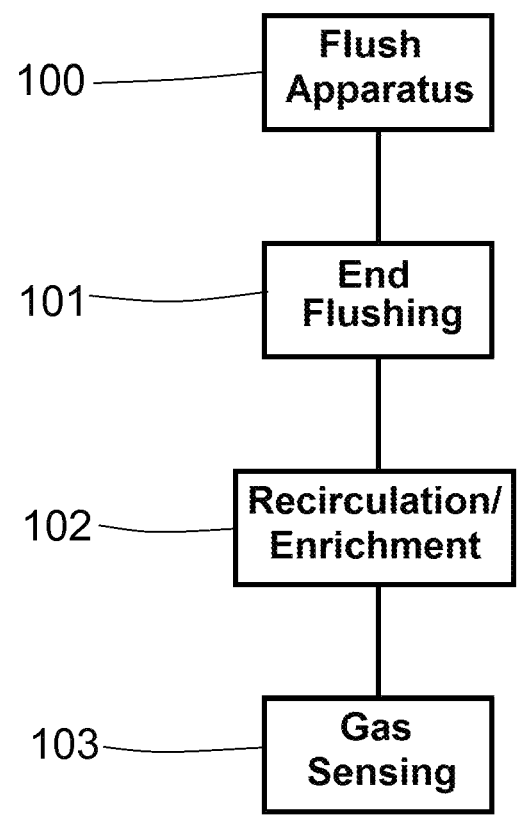
FIG. 5 shows a method for detection of gas.

A flow chart for a preferred embodiment of a method for detection of gases 4 in a high-voltage apparatus 3 filled with a liquid 2 is illustrated in FIG. 5, and the method is executed by the system 1 constructed in accordance with the first, second, third or fourth embodiment.

Step 100: Initially the system 1 is flushed. During operation of the second pump 10, the first pump 9 is switched off and thus blocks flow. The carrier gas 16 is drawn in through the inlet 5 then through the filter 15 into the first conduit 7.

In the first embodiment, the carrier gas 16 then passes through the measuring chamber 11 and the membrane 13 until it reaches the outlet 6 through the second pump 10 and the second conduit 8.

In the second embodiment the carrier gas 16 passes from the inlet 5 through the filter 15, the second pump 10, the first conduit 7, the membrane 13, and the measuring chamber 11, to arrive at the upstream end of the second connecting conduit 20 whence it reaches the outlet 6 through the second conduit 8.

In the third embodiment the carrier gas 16 traverses the membrane 13 and the measuring chamber 11 whence it reaches the outlet 6 through the second pump 10 and the second conduit 8.

In the fourth embodiment the carrier gas 16 then passes from the inlet 5 via the filter 15, the second pump 10, the first conduit 7, and the membrane 13 to the upstream part of the first connecting conduit 19 and then through the measuring chamber 11 until it reaches the outlet 6 via the second conduit 8.

Step 101: After a predetermined time or in dependence on the measurements of the gas sensor 12 in the measuring chamber 11 the flushing is concluded and the second pump 10 switched off. The parameters determined in the measuring chamber 11 at the cycle's end serve as a starting point or zero point for the further measurements.

Step 102: In the enrichment phase the first pump 9 is switched on, as a result of which the carrier gas 16 is recirculated through the system 1. The second pump 10 remains switched off and now blocks flow. The carrier gas 16 is moved in a closed circuit through the measuring chamber 11 and the membrane 13. Since the pressure inside the high-voltage apparatus 3 is greater than the pressure in the system 1, gases 4 pass from the insulating medium 2 through the membrane 13 permeable by gas molecules in one direction into the system 1. Enrichment of the carrier gas 16 thus takes place. The duration of the enrichment can be determined either by a fixedly preset time or by the measurements of the gas sensor 19 in the measuring chamber 11.

Step 103: After the enrichment phase, the amount and kind of gases 4 in the measuring chamber 11 are determined by the gas sensor 12. The system 1 is flushed after determination of the gases 4.

The described method can be carried out either continuously or, however, a few times per day. A discontinuous operation of the system 1 can lead to an increase in the service life of the gas sensor 12 used in the measuring chamber 11.

The invention claimed is:

1. A system for detecting a sample gas in a high-voltage apparatus filled with an insulating medium, the system comprising:
   a chamber;
   an inlet for taking in a carrier gas;
   an outlet for discharging the carrier gas;
   at least one gas sensor in the chamber for detecting the sample gas;
   first and second conduits between the chamber and the high-voltage apparatus;
   a first pump operable for moving the carrier gas through the chamber and the first conduit of the system and functioning as a closed valve when switched off;
   a semipermeable membrane connected in the high-voltage apparatus and to the second conduit, at least partly surrounded by the insulating medium, and at least partly exposed to a flow of the carrier gas, whereby the sample gas passes through the membrane into the carrier gas therein;
   a second pump for moving the carrier gas into the apparatus through the inlet and for moving the carrier gas out of the system through the outlet, the second valve also functioning as a closed valve when switched off; and
   a controller connected to the first and second pumps for, during operation of the first pump, blocking flow with the second pump and, during operation of the second pump, blocking flow with the first pump.

2. The system according to claim 1, wherein the inlet is connected to the first conduit.

3. The system according to claim 1, wherein the outlet is connected to a second conduit.

4. The system according to claim 1, wherein the first pump is in a first connecting conduit connecting an outlet of the measuring chamber with an inlet of the membrane or in a second connecting conduit connecting an outlet of the membrane with an inlet of the measuring chamber.

5. A method of operating the system of claim 1, the method comprising the steps of:
   first flushing a measuring chamber with a carrier gas by pumping the carrier gas with the second pump into the measuring chamber and out of the measuring chamber without flowing the carrier gas through a valve;
   thereafter pumping the carrier gas by the first pump out of the measuring chamber, through the gas-permeable membrane at least partly surrounded by the insulating medium and into the measuring chamber; and detecting the sample gas that has accumulated in the carrier gas flowing against the membrane in the measuring chamber.

6. The method according to claim 5, further comprising the step during the flushing of:
drawing the carrier gas through the first conduit and through the measuring chamber and purging the membrane through the second conduit.

7. The method according to claim 5, wherein the carrier gas is drawn in through a filter.

8. The method according to claim 5, further comprising the step of:
determining the amount or kind of the sample gas in the measuring chamber before or after the carrier gas is drawn out.

9. The method according to claim 5, further comprising the step of:
determining the amount or kind of the sample gas being detected in the measuring chamber before or after the carrier gas was drawn out.

10. A system for detecting a sample gas in a high-voltage apparatus filled with an insulating medium, the system comprising:
a measuring chamber;
a semipermeable membrane in the high-voltage apparatus, at least partly surrounded by the insulating medium, and holding a carrier gas such that the sample gas passes through the membrane into the carrier gas in the membrane;
at least one gas sensor in the chamber for detecting a concentration of the sample gas in the chamber;
first and second conduits extending between the chamber and the membrane and forming a circulation loop for the carrier gas through the membrane and through the chamber;
an inlet connected to the first conduit for taking in the carrier gas;
an outlet connected to the second conduit for discharging the carrier gas;
a first pump in the loop and functioning as a closed valve when switched off and for, when switched on, recirculating the carrier gas through the loop;
a second pump functioning as a closed valve when switched off and between one of the first and second conduits and either the inlet or the outlet for, when switched on, drawing the carrier gas into the loop through the inlet and for expelling the carrier gas out of the loop through the outlet; and
a controller for alternately operating the first and second pumps such that during operation of the first pump the carrier gas circulates through the loop while the second pump blocks flow out the outlet or into the inlet and during operation of the second pump the carrier gas is drawn in at the inlet and expelled out at the outlet while the first pump blocks recirculation of the carrier gas in the loop to flush the chamber.

11. The system according to claim 10, wherein the membrane is at least partly tubular or at least partly hose-like.

12. The system according to claim 10, wherein the membrane is at least partly spiral or at least partly meandering or at least partly helical.

13. The system according to claim 10, further comprising:
at least one thermoelement or at least one temperature sensor is or are provided in the measuring chamber.

14. The system according to claim 13, further comprising:
a controller connected to the temperature sensor, the thermoelement being controlled on the basis of the measurements of the temperature sensor.

15. The system according to claim 10, wherein the first conduit is provided with the inlet, and the second conduit is provided with the outlet, and
the measuring chamber is connected with the first conduit and by the membrane and the second conduit with the outlet.

16. The system according to claim 15, wherein the measuring chamber is provided between the first conduit and the membrane.

17. The system according to claim 15, wherein the second pump is provided in the first conduit or in the second conduit.

18. The system according to claim 15, wherein
if the second pump is in the first conduit it has an aspect ratio that is greater than the second conduit or greater than 100, 200, 500, 1000, 2000, 5000 or 10,000 or it has a flow resistance that is greater than that of the second conduit or that corresponds with that of a conduit with a constant inner diameter and an aspect ratio greater than 100, 200, 500, 1000, 2000, 5000 or 10,000;
if the second pump is in the second conduit it has an aspect ratio that is greater than the first conduit or greater than 100, 200, 500, 1000, 2000, 5000 or 10,000 or it has a flow resistance that is greater than that of the first conduit or that corresponds with that of a conduit with a constant inner diameter and an aspect ratio greater than 100, 200, 500, 1000, 2000, 5000 or 10,000.

19. The system according to claim 15, wherein the first conduit opens between the first pump and the membrane into a first connecting conduit that connects an outlet of the measuring chamber with an inlet of the membrane, or between the first pump and the measuring chamber into a second connecting conduit that connects an outlet of the membrane with an inlet of the measuring chamber.

* * * * *